United States Patent [19]

Eberbach

[11] Patent Number: 5,316,543
[45] Date of Patent: May 31, 1994

[54] MEDICAL APPARATUS AND METHODS FOR TREATING SLIDING HIATAL HERNIAS

[75] Inventor: Mark A. Eberbach, Tampa, Fla.

[73] Assignee: Cook Incorporated, Bloomington, Ind.

[21] Appl. No.: 619,886

[22] Filed: Nov. 27, 1990

[51] Int. Cl.$^5$ .............................................. A61F 2/00
[52] U.S. Cl. ...................................... 600/37; 128/897
[58] Field of Search ............... 600/37; 128/DIG. 23, 128/DIG. 25, 897–899; 623/11–14; 606/139, 144, 148, 150, 108

[56] References Cited

U.S. PATENT DOCUMENTS

| | | | |
|---|---|---|---|
| 3,875,928 | 4/1975 | Angelchik | 600/37 |
| 4,271,827 | 6/1981 | Angelchik | 600/37 |
| 4,271,828 | 6/1981 | Angelchik | 600/37 |
| 4,784,139 | 11/1988 | Demos | 606/148 |
| 4,796,603 | 1/1989 | Dahlke et al. | 128/899 |

Primary Examiner—Kyle L. Howell
Assistant Examiner—John P. Lacyk
Attorney, Agent, or Firm—Richard J. Godlewski

[57] ABSTRACT

Methods and apparatus for the repair of sliding hiatal hernias through laparoscopic techniques comprising a tubular sleeve; a conically shaped guide with an essentially pointed forward end positionable within the sleeve; a prosthesis coupled to the guide; and means for securing the prosthesis around the esophagus of a patient immediately beneath the patient's diaphragm whereby the prosthesis assumes a generally torus shape. The prosthesis may be pre-inflated and wherein the sleeve is axially splitable after the initiation of insertion of the guide. The prosthesis may be inflatable and further including a hose to inflate the prosthesis after positioning.

35 Claims, 3 Drawing Sheets

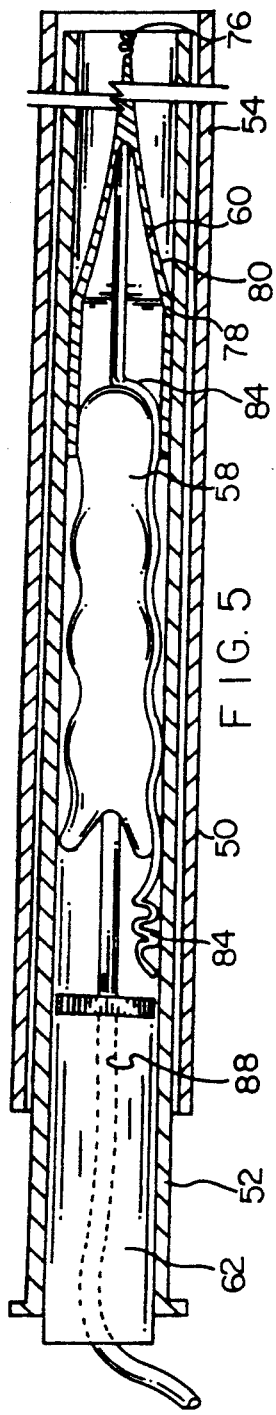
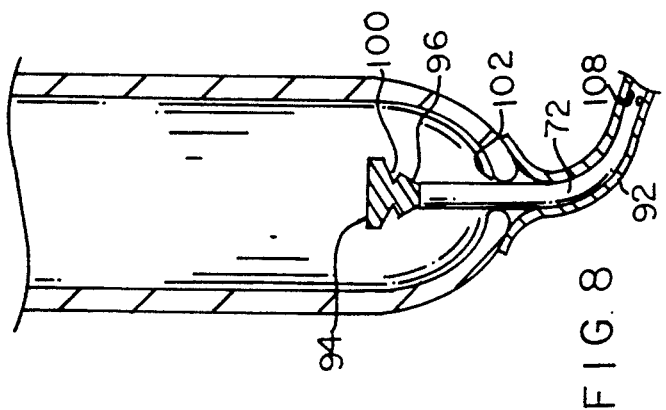
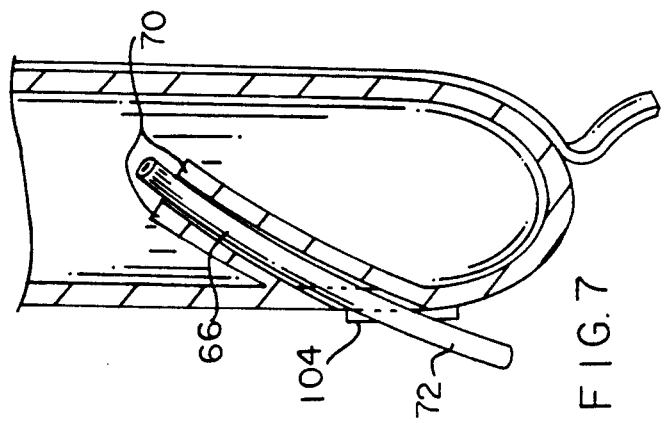
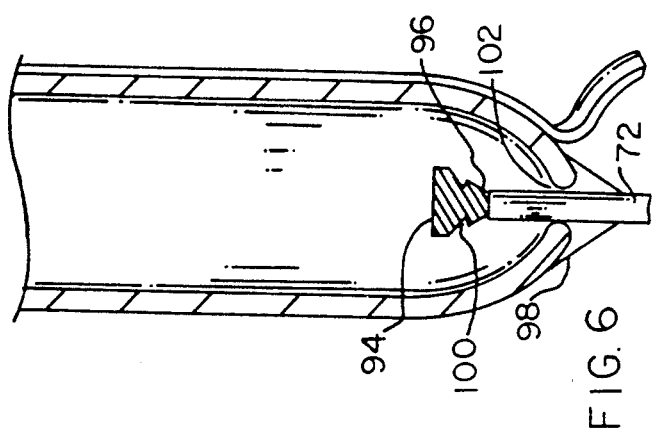

MEDICAL APPARATUS AND METHODS FOR TREATING SLIDING HIATAL HERNIAS

BACKGROUND OF THE INVENTION

1. Summary Of The Invention

This invention relates to a medical apparatus and methods for treating sliding hiatal hernias and, more particularly, to the treatment of an upwardly sliding stomach and esophagus to above the diaphragm with a laparoscopic approach and an associated inflatable, torus-shaped prosthesis.

2. Summary Of The Background Art

Gastroesophageal reflux is a significant problem for a large number of the population. The main cause of this is a sliding hiatal hernia. There are two types of hiatal hernia, a sliding and a paraesophageal. By far the majority, approximately 95%, of hiatal hernias are of the sliding variety. A sliding hiatal hernia occurs where the gastroesophageal junction and a proximal portion of the stomach displaces superiorly in to the mediastinum. The esophagus and the stomach slide into an opening of the diaphragm. The other type of hiatal hernia is a paraesophageal hiatal hernia where the gastroesophageal junction remains in its normal position but the main body or fundus of the stomach herniates through the hiatus to the left of the esophagus. With time, increasing amounts of the stomach move into the chest. This represents a life threatening situation and needs to be operated upon.

The sliding type of hiatal hernia often results in gastroesophageal reflux and reflux esophagitis. While this defect is present in a large portion of the general population, actual reflux esophagitis or discomfort is less common. Obesity, increasing weakness of the fascial attachments, chronic coughing, among others lead to this. A number of pharmaceutical agents can increase the risk of reflux.

The symptoms of sliding hiatal hernia are not caused by the hiatal hernia per se but are from the reflux that is present. Normally reflux is prevented by mechanical effects of a segment of the lower esophagus which remains intra abdominal and the lower esophageal sphincter. With increasing abdominal pressure, pressure is transmitted to the distal esophagus and thus reflux is prevented in the normal situation. When the sphincter is incompetent or the distal esophagus is not intraabdominal then reflux can occur. The long-term effects of gastroesophageal reflux is reflux esophagitis with esophogeal stricture and the possibility of carinoma of the esophagus. In addition with severe reflux multiple aspiration pneumonias are possible and even death.

Medical treatment is directed at weight loss, antacids and other anti reflux medications. Very often these are inadequate to alleviate the symptomology. The surgical treatment in the past has required a large abdominal or thoracic incision to correct the problem. Three common proceedures are a Hill gastopexi, a Nissen fundoplication and a Belsi Mark IV fundic wrap. Each of these basically accomplishes a restoration of a segment of intraabdominal esophagus generally four centimeters in length and also provides some means of securing the gastroesophageal junction in an appropriate position to prevent reflux. Another procedure which has been found to be effective is the placement of a prosthesis about the esophagus to maintain an intraabdominal segment. This prosthesis is called an Angelchik prosthesis manufactured by Mentor Corporation of Goleta, Calif. This procedure is a less invasive procedure, does require a large intraabdominal incision but requires less in the way of dissection about the esophagus.

Although common, the standard operational procedures for repair of sliding hiatal hernias is undesireable, lengthy, and consequently costly. Such procedures also require a large incision with excessive dissection of normal tissue, cause excessive pain and discomfort to the patient, involve unacceptably long recovery and work disability time.

Accordingly, it is an object of the present invention to provide methods and apparatus for the repair of sliding hiatal hernias through laparoscopic techniques comprising a tubular sleeve; a conically shaped guide with an essentially pointed forward end positionable within the sleeve; a prosthesis coupled to the guide; and means for securing the prosthesis around the esophagus of a patient immediately beneath the patient's diaphragm whereby the prosthesis assumes a generally torus shape wherein the prosthesis may be pre-inflated or inflatable and wherein the sleeve is axially splitable after the initiation of insertion of the guide or wherein the prosthesis may be inflatable and further including a hose to inflate the prosthesis after positioning.

It is the further object of the present invention to employ laparoscopic techniques for the repair of sliding hiatal hernias.

It is a further object of the invention to reduce the length of the incision, along with the unnecessary disection of normal tissue, for the repair of sliding hiatal hernias.

It is a further object of the present invention to minimize the time and cost of sliding hiatal hernia operations along with the patient's pain, discomfort and recovery time associated therewith.

It is the further object of the present invention to abate sliding hiatal hernias.

It is a further object of the invention to utilize a sleeve to introduce an inflatable prosthesis for the repair of sliding hiatal hernias.

It is a further object of the invention to utilize an axially splitable sleeve to introduce a pre-filled or inflatable or other prosthesis for the repair of sliding hiatal hernias and other intraabdominal procedures.

The foregoing has outlined some of the more pertinent objects of the invention. These objects should be construed to be merely illustrative of some of the more prominent features and applications of the intended invention. Many other beneficial results can be attained by applying the disclosed invention in a different manner or by modifying the invention within the scope of the disclosure. Other objects and a fuller understanding of the invention may be had by referring to the summary of the invention and the detailed description of the preferred embodiments in addition to the scope of the invention defined by the claims taken in conjunction with the accompanying drawings.

SUMMARY OF THE INVENTION

This invention is defined by the appended claims with specific embodiments shown in the attached drawings. For the purposes of summarizing the invention, the invention may be incorporated into an improved apparatus for the repair of sliding hiatal hernias through laparoscopic techniques comprising a tubular sleeve; a conically shaped guide with an essentially pointed forward end positionable within the sleeve; a prosthesis coupled to the guide; and means for securing the prosthesis around the esophagus of a patient immediately beneath the patient's diaphragm whereby the prosthesis assumes a generally torus shape. The prosthesis may be pre-inflated and wherein the sleeve is axially splitable after the initiation of insertion of the guide. The prosthesis may be inflatable and further including a hose to inflate the prosthesis after positioning.

The invention may also be incorporated into a method for the repair of sliding hiatal hernias through laparoscopic techniques comprising the steps of providing a tubular sleeve; providing a conically shaped guide with an essentially pointed forward end; providing a prosthesis coupled to the guide; inserting the guide into the sleeve; advancing the guide and prosthesis to interior of the patient; positioning the prosthesis around the esophagus of a patient immediately beneath the patient's diaphragm whereby the prosthesis assumes a generally torus shape; and securing the coupling means to properly shape and position the prosthesis. The prosthesis may be pre-inflated and further including the step of axially splitting the sleeve after the initiation of insertion of the guide. The prosthesis may be inflatable and further including the step of inflating the prosthesis with a hose after positioning.

The invention may also be incorporated into apparatus for the repair of sliding hiatal hernias through laparoscopic techniques comprising a tubular sleeve separable into two linear halves; a conically shaped guide with an essentially pointed forward end of a diameter whereby the forward end of the guide may be inserted within the sleeve; a prosthesis having a forward portion coupled to a trailing portion of the guide; and means at the ends of the prosthesis for securing the prosthesis around the esophagus of a patient immediately beneath the patient's diaphragm whereby the prosthesis assumes a torus shape. The prosthesis is pre-inflated and wherein the sleeve is axially splitable after the initiation of insertion of a portion of the guide. The apparatus further includes a plurality of recesses extending axially along the length of the sleeve. The apparatus further includes flanges on the proximal end of the sleeve.

The invention may also be incorporated into a method for the repair of sliding hiatal hernias through laparoscopic techniques comprising providing a tubular sleeve; providing a conically shaped guide with an essentially pointed forward end; providing a pre-inflated prosthesis coupled to the guide; initially inserting the guide into the sleeve; axially splitting the sleeve after the initiation of insertion of the guide; removing the split sleeve; advancing the guide and prosthesis to interior of the patient; positioning the prosthesis around the esophagus of a patient immediately beneath the patient's diaphragm whereby the prosthesis assumes a generally torus shape; and securing the coupling means to properly shape and position the prosthesis.

The invention may also be incorporated into apparatus for the repair of sliding hiatal hernias through laparoscopic techniques comprising a tubular sheath; a prosthesis located within and moveable with respect to the sheath; a conically shaped guide within the sheath adjacent to its forward end; coupling means secured to the leading and trailing ends of the prosthesis; and a plunger located partially within the sheath adjacent to its rearward end for pushing the guide member from the sheath. The plunger has a circular hole therethrough with a filler hose extending through the hole for inflating the prosthesis. The hose extends to interior of the prosthesis through a self sealing valve. The self sealing valve may be at the trailing end of the prosthesis. The coupling means may be ribbons and the hose extending coaxially therethrough. The self sealing valve may be on a peripheral face of the prosthesis.

The invention may also be incorporated into a method for repairing sliding hiatal hernias through laparoscopic techniques comprising providing a tubular sheath; positioning an inflatable prosthesis within and moveable along the length of the sheath; positioning a conically shaped guide within the sheath with an essentially pointed end at its forward end; positioning a plunger partially within the sheath adjacent to its rearward end; inserting the sheath into a sleeve extending from exterior to interior of a patient; pushing the plunger to move the guide member from the sheath; positioning the prosthesis around the esophagus of the patient immediately beneath the diaphragm; and coupling the prosthesis in position by ties at the opposite ends of the prosthesis.

The invention may also be incorporated into a system for the repair of sliding hiatal hernias through laparoscopic techniques comprising a trocar sleeve; a tubular sheath positionable within the sleeve; a prosthesis located within and moveable with respect to the sheath; a conically shaped guide within the sheath adjacent to its forward end; coupling means secured to the leading and trailing ends of the prosthesis; and a plunger located partially within the sheath adjacent to its rearward end for pushing the guide member from the sheath, a circular hole through the plunger with a filler hose extending through the hole for inflating the prosthesis, the hose extending to interior of the prosthesis through a self sealing valve, the valve being located at the trailing end of the prosthesis.

The invention may also be incorporated into an inflatable prosthesis for repair of a sliding hiatal hernia positionable around a patient's esophagus immediately beneath the diaphragm, the prosthesis being hollow and formed of an elastomeric material, the prosthesis having a self sealing valve for its inflation and coupling means at its opposite ends for conforming the prosthesis into a torus shape.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific embodiments may be readily utilized as a basis for modifying or designing other methods and structures for carrying out the same purposes of the present invention. It should also be realized by those skilled in the art that such equivalent methods and structures do not depart from the spirit and scope of the invention as set forth in the appended claims.

DESCRIPTION OF THE DRAWINGS

For a fuller understanding of the nature and objects of the invention, reference should be had to the following detailed description taken in conjunction with the accompanying drawings in which:

FIG. 5 is a side elevational view of an alternate embodiment of the invention designed to position an inflatable prosthesis around the esophagus immediately beneath the diaphragm with parts of the apparatus being broken away to show certain internal construction thereof.

FIGS. 6, 7 and 8 are sectional views of a portion of the prosthesis of the prior Figures including the valves, hoses, etc. for filling the prosthesis after its placement.

Similar reference numerals refer to similar parts throughout the various Figures.

DETAILED DESCRIPTION OF THE INVENTION

Figure 1:
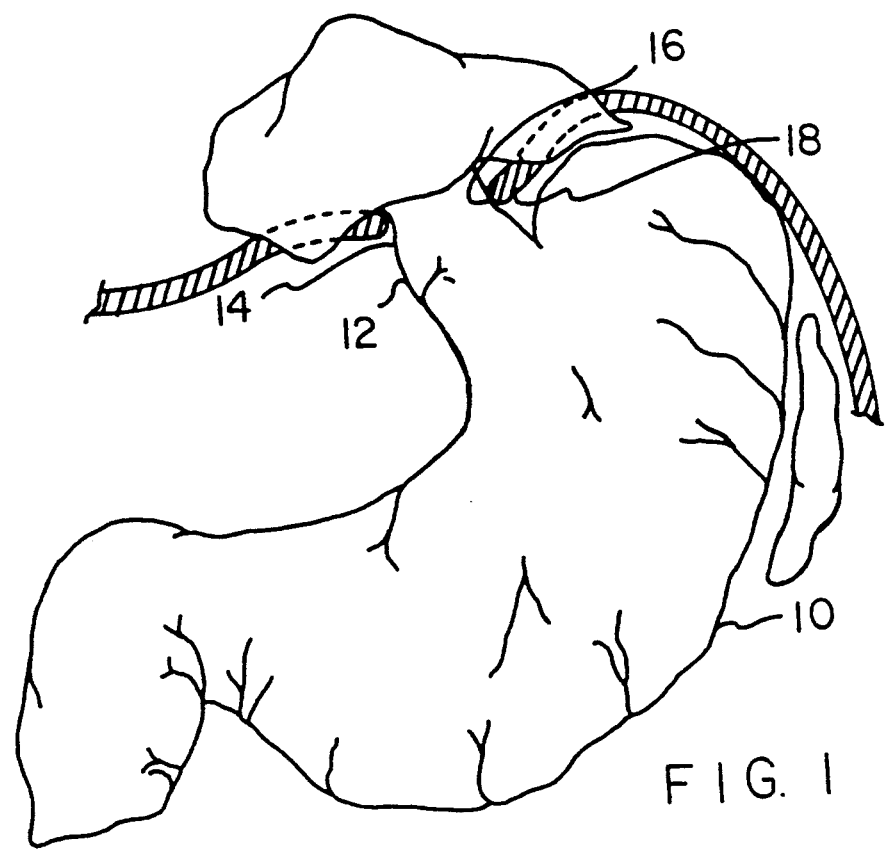
FIG. 1 shows a portion of the stomach including the stomach and esophagus as well as the diaphragm whereat hiatal hernias normally occur.
Figure 2:
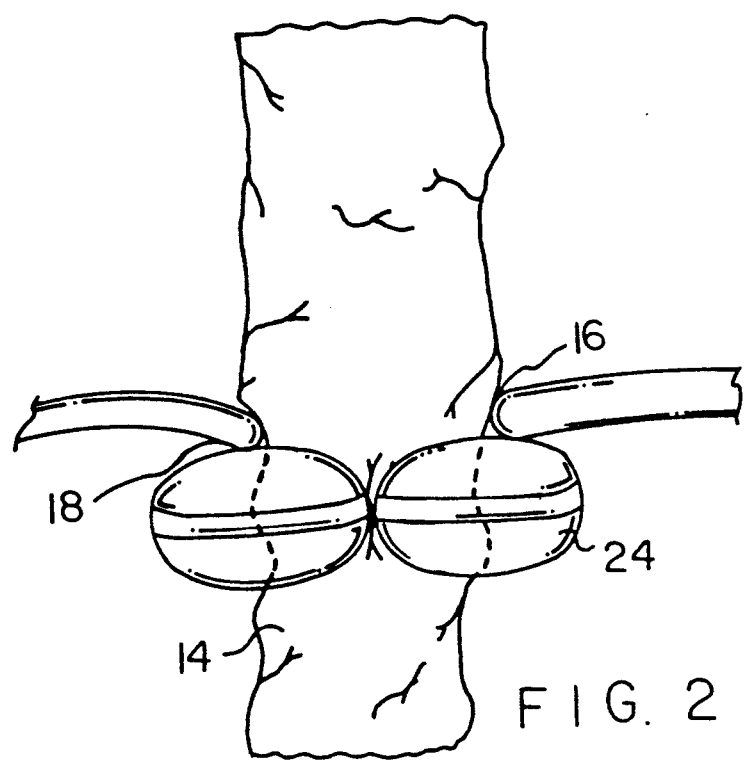
FIG. 2 is an enlarged portion of the stomach and esophagus including the diaphragm illustrating the placement and positioning of the prosthesis for precluding the upward movement of the upper portion of the stomach to above the diaphragm.
Figure 4:
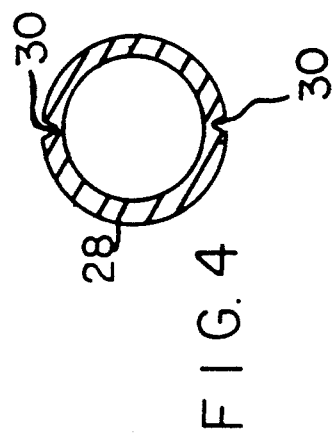
FIG. 4 is a sectional view of the axially splitable sleeve for use in association with the apparatus of the FIG. 3 embodiment.

As shown in FIG. 1 is that portion of the stomach 10 including the upper portion 12 of the stomach and the lower portion of the esophagus 14 including the opening 16 in the diaphragm 18 whereat sliding hiatal hernias occur. The upper portion of the stomach, for whatever reason, sometimes moves upwardly above the opening in the diaphragm walls through which it passes. This thereby creates a medical condition which may require surgery to correct and to preclude its occurrence. The present invention includes laparoscopic delivery apparatus 22, a system, for the introduction of a prosthesis 24 around the esophagus immediately beneath the diaphragm to preclude the occurrence of the sliding hiatal hernia.

The primary embodiment of the invention may be understood by reference to the apparatus of FIGS. 1 through 4. According to that embodiment, a trocar is used in the conventional manner to insert a tubular sleeve 28. The sleeve, however, is designed and constructed with a pair of diametrically opposed axial recesses 30. The recesses allow the sleeve to be split into two linear pieces upon the application of a radial force. Two flanges 32 are formed on the proximal end of the sleeve for being grasped during the splitting of the sleeve. Miniaturized sleeves which are splitable are commercially available by Cook International Corporation. Such known sleeves are for intravascular usage.

Positionable into the sleeve is a guide 36. The guide is of an elongated conical configuration with a generally pointed leading end 38. The guide is positionable through the sleeve from external of a patient to internal of a patient. The leading edge of the inserted guide may be grasped by a surgeon through a forceps from an additional laparoscopic opening. When so grasped, the surgon may pull the guide and trailing components, including a pre-filled prosthesis 24, into proper position to internal of a patient and around the esophagus. Thereafter the surgeon will tie the ribbons 40 of the prosthesis to hold the prosthesis in proper position. Ribbons or other tying or coupling devices extend from each end of the prosthesis for tying purposes. The prosthesis is preferably a modified Angelchik prosthesis in common use today and as fully described in the medical literature. Angelchik prosthesis are commercially available by Mentor Corporation.

Extending proximally from the pointed leading end 38, the walls of the guide 36 extend outwardly in a conical configuration terminating at a base end 42. The walls are thin to allow for a bending of the guide during manipulation by a surgeon through forceps. The guide is a cone shaped member having a pointed forward end adapted to pierce tissue attached to the external periphery of the esophagus in the region to receive the prosthesis. The hollow walls also define a space 44 for the receipt of the distal or leading end of the prosthesis 24. The ribbon at the leading end of the prosthesis is attached to the interior of the guide 36. In this manner, the pulling of the guide will pull the prosthesis 24.

The preclusion of improper movement of the positioned prosthesis is effected by the textured exterior surface of the prosthesis. Such textured surface also allows in-growth of flesh thereadjacent to better incorporate the prosthesis.

In operation and use, the leading end 38 of the guide 36 is inserted into the proximal end of the sleeve 28. As the surgeon pushes the guide forwardly through the sleeve and into the patient, the increased diameter of the guide and prosthesis will preclude further axial movement due to the lesser diameter of the sleeve. The sleeve is about 20 centimeters in length with an inside diameter of about 1 centimeter. The guide is about 30 centimeters in length. The prosthesis and base of the guide are about 2 centimeters in diameter which is greater than the inside diameter of the sleeve. The circumference of the sleeve is sufficiently small so as to minimize the size of the incision while allowing the introduction of the prosthesis and its manipulation. This sleeve is fabricated of a relatively rigid plastic, preferably polyethylene, to retain its shape even during the application of moderate forces tending to cause its defamation.

In order to allow further movement of the guide and prosthesis into the sleeve and the patient, the surgeon will then axially split the sleeve beginning at the proximal end. This is affected by grasping the flanges and applying a radial force. The sleeve is split further until it is fully separated into two pieces with the leading edge of the guide inserted into the patient. The sleeve, being split into two pieces, may then be removed from the patient and discarded.

The surgeon then employs forceps from another laparoscopic opening in the patient to pull the guide and prosthesis into the patient. The opening in the patient acts as a lubricious surface through which the lubricious guide and prosthesis may pass with the pre-inflated prosthesis necking down as it moves through the opening. With the prosthesis located within the patient, the surgeon may use an additional laparoscopic opening or openings to finally position and tie the prosthesis in final position.

After proper positioning, the guide is cut perpendicularly to its axis to cut the leading coupling line and to cut the guide in two. The portions of the guide may then be removed by the surgeon by the use of forceps in a conventional laparoscopic manner. In this manner, with the prosthesis in place, its position is secured by tying the two coupling lines together in a knot to effectively make a permanent coupling. An annular recess or other indicia around the circumference of the guide identifies the area of the guide to be cut so as to free the leading line from the guide.

The trailing ribbon of the prosthesis will permit a second sleeve of conventional construction to be placed over it with the ribbon within the sleeve opening. The sleeve will then be slid toward and into the incision with the ribbon functioning as a guide. The second sleeve will thus be inserted into the patient's incision, extending from internal to external thereof, for acting as a supplemental entry point for further laparoscopic procedures.

Conventional prosthesis normally have radiopaque markings or other indicia so that the surgeon may observe the location and orientation of the prosthesis during or after an operation as through an x-ray unit. The guide and other components are likewise preferably provided with such radiopaque markings. Such markings may be added after fabrication or included integral therewith during the fabrication process. The surgeon's taks is thus simplified during an operation and after.

As a further modification to the primary embodiment, the prosthesis may be inserted in an unfilled condition and then subsequently inflated as described hereinafter.

In the alternate embodiment of the invention, a modified delivery apparatus 50 is employed which is most clearly shown in FIG. 5. The delivery apparatus is a system which includes a sheath 52 formed as a thin walled cylinder about 20 centimeters in length, the approximate length of the sleeve 54. It has an external diameter of about 1.0 centimeters. The length is to allow the sheath 52 and its contents to be positioned within a conventional trocar sleeve 54 with its forward end positioned adjacent to the region to be repaired while its rearward end is outside of the patient for manipulation by the surgeon. The circumference of the sleeve and sheath are sufficiently small so as to minimize the size of the incision while allowing the introduction of the prosthesis and its manipulation. This sheath is fabricated of a relatively rigid plastic, preferably polyethylene, to retain its shape even during the application of moderate forces tending to cause its defamation.

Located within the sheath are the internal components. Such internal components include the centrally located prosthesis 58, a forwardly positioned guide member 60 located within the forward end of the sheath and a rearwardly positioned plunger 62 adjacent to the rear end of the sheath and extending outwardly thereof for manipulation by the surgeon during the surgical procedure.

The prosthesis is a hollow, thin-walled, inflatable cylinder with circular closures at its forward and rearward ends. It includes an inflation valve 66 located in the central portion of the rearward end or, in an alternate embodiment, located along a circumferential face adjacent to the rearward end. No matter where positioned, the valve is provided with self sealing members illustrated in the preferred manner as flapper sheets 70 deformable upon the introduction and removal of a filling hose 72 for effecting the filling of the prosthesis after being positioned during operation and use. The sheet has memory to return to the normal or closed position where it will remain after being filled with a fluid which applies pressure and holds the flap in its closed orientation to preclude leakage. Alternate self sealing valves could be readily utilized.

The prosthesis itself is formed of an elastomeric material, preferably silicone. It is adapted to be manipulated by the surgeon into its essentially circular or generally torus-shaped configuration about the esophagus beneath the diaphragm. The prosthesis normally has an outer circle diameter of 7 centimeters and an inner circle diameter of about 2.5 centimeters when contoured as a torus with about a 2 centimeter cross sectional diameter after inflation and with a thickness of about 0.1 centimeters. The material, size and shape of the prosthesis are sufficient to allow it to remain in its intended configuration unless acted upon by external forces during implantation and/or use.

Figure 3:
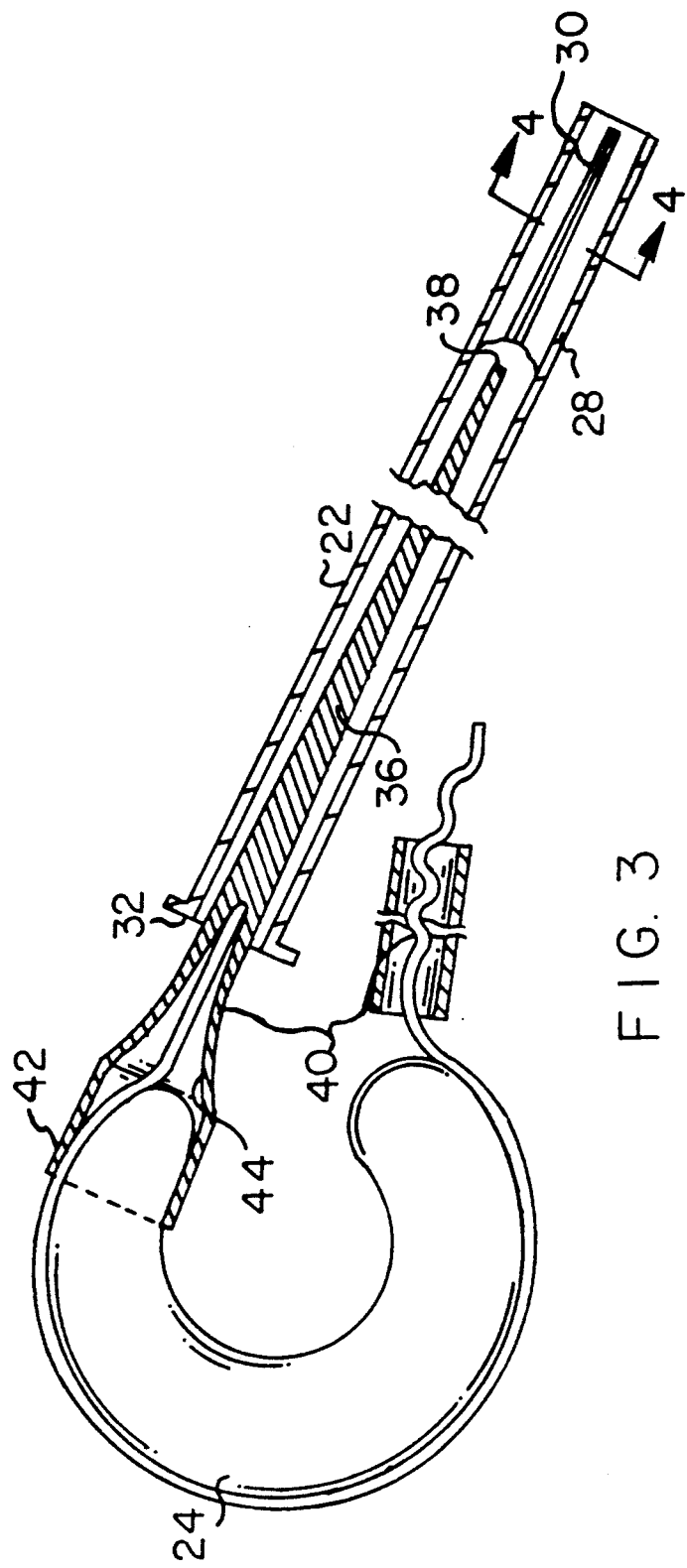
FIG. 3 is a side elevational view of a sleeve and the primary embodiment of the apparatus which is designed to position a pre-filled prosthesis around the esophagus immediately beneath the diaphragm with parts of the apparatus being broken away to show certain internal construction thereof.

Located forwardly of the prosthesis 58 is the guide or guide member 60. The guide is a cone shaped member having a pointed forward end 76 adapted to pierce tissue attached to the external periphery of the esophagus in the region to receive the prosthesis. The forward extent of the guide may be straight as shown in FIG. 3 or it may be spiralled in a cork screw configuration as shown in FIG. 5, similar to a coiled rope or hose. If configured as in FIG. 5, the point would be straightened out by the surgeon after movement of the guide from the sheath. The guide is normally about 30 centimeters in length having a diameter of about 3 millimeters at the tip end and about 1.0 centimeters at its base end 78. The prosthesis is about 2 centimeters in diameter when inflated. The diameter of the base is about 1.0 centimeter for the inflatable embodiment as described hereinafter. Its interior is hollowed out 80 in an internal conical configuration for receiving a the forward coupling line 84 secured at its rearward end to the forward face of the prosthesis and at its forward end to the forward end of the opening in the guide. The guide is fabricated of an elastomeric material, preferably polyethylene. It thus may be bent by the surgeon when pushed from the sheath or pulled around the esophagus during implantation.

At the rearward end of the sheath is the plunger 62. The plunger is a cylindrical member adapted to be positioned at the rearward end of the sheath 52 with its rearward end extending rearwardly out of the sheath. The forward end of the plunger is adapted to push the prosthesis and guide from the sheath after the sheath has been positioned in the patient in the region beneath the diaphragm. The plunger is fabricated of a rigid polymeric material, preferably polyethylene. It is adapted to retain its shape at all times even when its rearward end is pushed forwardly into the sheath by the surgeon to move the guide out of the sheath.

Centrally located through the plunger 62 is a hole 88 for receiving the filler hose 72. The filler hose has a rearward end adapted to be coupled to a source of pressurized fluid with its forward end adapted to be coupled through the self sealing valve 66 of the prosthesis. The filler tube is flexible and of a size, about 4 millimeters in outside diameter, whereby its forward end may be received and passed outwardly from the hole in the plunger through which it passes. The forward end of the filler hose is coupled to the self sealing valve at the rearward face of the prosthesis whereby upon pulling of the guide, the coupling line will pull the prosthesis and, concurrently therewith, the coupling between the leading edge of the filler hose and a self sealing valve will allow the filler hose to be pulled along with the prosthesis.

The plunger and rearward end of the guide have their radially exterior surfaces in close proximity to the interior surface of the sheath. As a result, when the plunger is pushed forward, the air entrapped therebetween will increase in pressure to thereby advance the guide forwardly. The leading edge of the guide will thus be pushed sufficiently so that it will be moved outside of the sheath for being grasped and advanced by the surgeon manipulating a forceps.

In order to use the apparatus of the present invention, the operating laparoscope is utilized. The sheath and its contents are manipulated inwardly and outwardly thereof for effecting the appropriate procedures. After dissection, other laparoscopic incissions in the abdomen are made for placement of a second or third or further sleeves or devices as may be required by the procedure. These additional incisions allow for additional instruments for dissection, prosthesis introduction, observation, guide and prosthesis manipulation, etc.

To position the prosthesis in its orientation at the intended region, the sleeve is positioned appropriately and the plunger is moved forwardly by the surgeon to move the prosthesis and guide forwardly until the leading edge of the guide is outside of the sheath. In this manner, the surgeon may grip the leading edge of the guide with a forceps from a further laparoscopic entry point to pull the guide, prosthesis, and associated components into the intended location around the esophagus beneath the diaphragm. During such procedure, the guide will act to pierce and bluntly dissect any tissue in its path of movement as is required to effect proper placement of the prosthesis. In addition to, or as an alternative, such extraneous tissue may be cut by the surgeon through a further laparoscopic entry through conventional surgical techniques.

After proper positioning, the guide is centrally cut perpendicularly to its axis adjacent to mid-point to cut the leading coupling line and to cut the guide in two. The portions of the guide may then be removed by the surgeon by the use of forceps in a conventional laparoscopic manner. In this manner, with the prosthesis in place and uninflated, its position is secured by tying the two coupling lines together in a know to effectively make a permanent coupling. In the alternative, the prosthesis may be inflated and then tied.

Thereafter, the prosthesis is filled to provide a mechanical barrier and prevent herniation. Filling the prosthesis is effected through the filler hose which has been coupled to the trailing edge of the prosthesis extending into the self sealing valve. Coupling may be effected at the time of fabrication of the system in which case the self sealing valve would be on the trailing end of the prosthesis. In the alternative, the filler hose may be separate from the prosthesis during the positioning of the prosthesis. In such case, the surgeon will push the leading edge of the hose through the sleeve whereby the leading edge may be grasped by a surgeon using laparoscopic forceps for inserting the hose into the self sealing valve. In this alternate procedure, the self sealing valve may be in the end of the prosthesis or along a circumferential wall thereof.

When a predetermined amount of volume has been applied by a pump at the trailing end of the filler hose, the pumping of the fluid is stopped and the hose end removed from the prosthesis. The preferred fluid is a saline solution. The flapper sheet will then receive sufficient back pressure from the fluid inside the prosthesis to effect a permanent sealing of the fluid within the prosthesis. The mechanical force is sufficient to preclude inadvertent movement of the stomach with respect to the diaphragm. With the prosthesis tied in position and filled with fluid, the tube is removed and the incisions closed to complete the procedure.

A modification of the ribbons and valves may be seen in FIG. 8. According to that embodiment, the hose is coupled to the prosthesis through a self sealing valve 66 as described above. The ribbon 92 is, however, hollow along its length with the hose 72 extending coaxially therethrough. In this manner, when the hose is withdrawn after filling the prosthesis, the tying of the ribbons will seal the hose and function as a secondary seal for the prosthesis.

Variations in the self sealing valves can be seen by reference to FIGS. 6, 7 and 8. FIG. 6 employs a stopper 94 of an elastomeric material coupled to the end of the hose. A separable coupling 96 therebetween is effected through a reduced annular area. A plurality of breakable tether threads 98 couple the prosthesis to the hose for precluding separation while manipulation positioning and filling. After inflation, the hose is withdrawn from the prosthesis by pulling the hose axially with sufficient force to break the tether threads or by cuting them and seat an annular recess 100 of the stopper in the orifice 102 of the prosthesis.

The FIG. 7 embodiment functions with a flapper valve as described above. In addition, a washer 104 is coupled to the hose at its inner peripheral surface. A flat surface of the washer is coupled to the prosthesis. Coupling is by welding, adhesion, or the like to ensure that the hose stays joined to the prosthesis during manipulation, positioning, and filling. The coupling of the hose to the washer is stronger than the coupling of the washer to the prosthesis so that after filling, an axial pulling of the hose will separate the hose and washing from the prosthesis.

The FIG. 8 embodiment, with the coaxial ribbon described above, employs a stopper 94 similar to that in the FIG. 6 embodiment. Coupling between the prosthesis and hose is at a location along their common axial extent as by a weld 108 or adhesive or the like. Axial pulling of the hose separates it from the ribbon and also seats the stopper.

Those embodiments employing a stopper are preferably provided with strengthening of the prosthesis around the orifice 102 to ensure a more positive sealing of the prosthesis by the stopper. Such strengthening is done by excess material around the orifice or by otherwise providing the orifice with a stronger or less resilient material or added material of greater strength.

The two embodiments of the present invention may be utilized by surgeons carrying out new laparoscopic procedures for repairing hiatal hernias.

The present invention having been thus described, it should be apparent that modifications could be made to the various components of the apparatus and methods of the present invention, as would occur to one of ordinary skill in the art without departing from the spirit and scope of the present invention.

Now that the invention has been described,
What is claimed is:
1. Apparatus for the repair of sliding hiatal hernias through laparoscopic techniques comprising:
 a tubular sleeve;
 a conically shaped guide with an essentially pointed forward end positionable within the sleeve;
 a prosthesis coupled to the guide; and
 means for securing the prosthesis around the esophagus of a patient immediately beneath the patient's diaphragm whereby the prosthesis assumes a generally torus shape.

2. The apparatus as set forth in claim 1 and further including radiopaque indicia on the guide.

3. The apparatus as set forth in claim 1 and further including a marking on the guide to indicate the region to be cut to free the guide from the means for securing.

4. The apparatus as set forth in claim 1 wherein the external surface of the prosthesis is textured.

5. The apparatus as set forth in claim 1 wherein the prosthesis is pre-inflated and wherein the sleeve includes a weakened axial extent so that the sleeve is axially split after the initiation of insertion of the guide.

6. The apparatus as set forth in claim 1 wherein the prosthesis is inflatable and further including a hose to inflate the prosthesis after positioning.

7. A method for the repair of sliding hiatal hernias through laparoscopic techniques comprising:
providing a tubular sleeve;
providing a conically shaped guide with an essentially pointed forward end;
providing a prosthesis coupled to the guide, the prosthesis having coupling means;
inserting the guide into the sleeve;
inserting the sleeve into the patient;
advancing the guide and prosthesis to interior of the patient;
positioning the prosthesis around the stomach of a patient immediately beneath the patient's diaphragm whereby the prosthesis assumes a generally torus shape; and
securing the coupling means to properly shape and position the prosthesis.

8. The method as set forth in claim 7 wherein the prosthesis is pre-inflated and further including the step of axially splitting the sleeve after the initiation of insertion of the guide.

9. The method as set forth in claim 7 wherein the prosthesis is inflatable and further including the step of inflating the prosthesis with a hose.

10. Apparatus for the repair of sliding hiatal hernias through laparoscopic techniques comprising:
a tubular sleeve separable into two linear halves;
a conically shaped guide with an essentially pointed forward end of a diameter to facilitate insertion of the forward end of the guide into the sleeve;
a prosthesis having a forward portion coupled to a trailing portion of the guide; and
means at the ends of the prosthesis for securing the prosthesis around the esophagus of a patient immediately beneath the patient's diaphragm whereby the prosthesis assumes a torus shape.

11. The apparatus as set forth in claim 10 wherein the prosthesis is pre-inflated and wherein the sleeve includes a weakened axial extent so that the sleeve is axially split after the initiation of insertion of a portion of the guide.

12. The apparatus as set forth in claim 11 and further including a plurality of recesses extending axially along the length of the sleeve.

13. The apparatus as set forth in claim 12 and further including flanges on the proximal end of the sleeve.

14. A method for the repair of sliding hiatal hernias through a laparoscopic techniques comprising:
positioning a tubular sleeve in a patient's incision;
providing a conically shaped guide with an essentially pointed forward end;
providing a pre-inflated prosthesis coupled to the guide, the prosthesis having coupling means;
initially inserting the guide into the sleeve;
axially splitting the sleeve after the initiation of insertion of the guide;
removing the split sleeve;
advancing the guide and prosthesis to interior of the patient;
positioning the prosthesis around the esophagus of a patient immediately beneath the patient's diaphragm whereby the prosthesis assumes a generally torus shape;
providing coupling means with ties; and
securing the coupling means to properly shape and position the prosthesis.

15. The method as set forth in claim 14 and further including the step of providing a trailing line on the prosthesis and utilizing the trailing line to guide a supplemental sleeve into the patient's incision.

16. Apparatus for the repair of sliding hiatal hernias through laparoscopic techniques comprising:
a tubular sheath having a forward end and rearward end;
a prosthesis with a leading end and a trailing end, the prosthesis located within and movable with respect to the sheath;
a conically shaped guide within the sheath adjacent to the forward end of the sheath;
coupling means secured to the leading and trailing ends of the prosthesis; and
a plunger located partially within the sheath adjacent to the rearward end of the sheath for pushing the guide from the sheath.

17. The apparatus as set forth in claim 16 wherein the sheath, prosthesis, guide, coupling means and plunger are all prepackaged as a unit.

18. The apparatus as set forth in claim 16 wherein the plunger has a circular hole therethrough with a filler hose extending through the hole for inflating the prosthesis.

19. The apparatus as set forth in claim 18 wherein the hose extends to interior of the prosthesis through a self sealing valve.

20. The apparatus as set forth in claim 19 wherein the self sealing valve is at the trailing end of the prosthesis.

21. The apparatus as set forth in claim 19 wherein the coupling means are ribbons and the hose extends coaxially therethrough.

22. The apparatus as set forth in claim 19 wherein the self sealing valve is on a peripheral face of the prosthesis.

23. A method for repairing sliding hiatal hernias through laparoscopic techniques comprising:
providing a tubular sheath having a forward end and a rearward end;
positioning an inflatable prosthesis within and movable along the length of the sheath, the prosthesis having a leading end and a trailing end;
positioning a conically shaped guide with an essentially pointed leading end within the sheath;
positioning a plunger partially within the sheath adjacent to the rearward end of the sheath;
inserting the sheath into a sleeve extending from exterior to interior of a patient;
pushing the plunger to move the guide from the sheath;

positioning the prosthesis around the esophagus of the patient immediately beneath the diaphragm; and coupling the prosthesis in position by ties at the leading and trailing ends of the prosthesis.

24. A system for the repair of sliding hiatal hernias through laparoscopic techniques comprising:

a trocar sleeve having a forward end and a rearward end;

a tubular sheath positionable within the sleeve, the sheath having a forward end and a rearward end;

a prosthesis located within and movable with respect to the sheath, the prosthesis having a leading end and a trailing end;

a conically shaped guide within the sheath adjacent to the forward end of the sheath;

coupling means secured to the leading and trailing ends of the prosthesis; and a plunger located partially within the sheath adjacent to the rearward end of the sheath for pushing the guide from the sheath, a coaxial circular hole through the plunger with a filler hose extending through the hole for inflating the prosthesis, the hose extending to interior of the prosthesis through a self sealing valve, the valve being located at the trailing end of the prosthesis.

25. An inflatable prosthesis for repair of a sliding hiatal hernia positionable around a patient's esophagus immediately beneath the diaphragm, the prosthesis being hollow and formed of an elastomeric material, the prosthesis having a self sealing valve for its inflation and coupling means at its opposite ends for retaining the prosthesis into a torus shape.

26. The prosthesis as set forth in claim 25 and further including a filling hose and tether means separably coupling the prosthesis and the hose.

27. The prosthesis as set forth in claim 25 and further including a filling hose and a washer separately coupling the prosthesis and the hose.

28. The prosthesis as set forth in claim 25 and further including a hose with a discharge orifice on a peripheral side thereof and a stopper releasably secured to the end of the hose of self seal the valve upon removal of the hose from the prosthesis.

29. Apparatus for the repair of sliding hiatal hernias through laparoscopic techniques comprising:

a tubular sleeve;

a conically shaped guide with an essentially pointed forward end positionable within the sleeve;

a prosthesis coupled to the guide; and means for securing the prosthesis.

30. The apparatus as set forth in claim 29 wherein the prosthesis is pre-inflated.

31. The apparatus as set forth in claim 29 wherein the prosthesis is inflatable.

32. Apparatus for use in laparoscopic techinques comprising:

a tubular sleeve;

a conically shaped guide positionable within the sleeve;

an inflatable prosthesis coupled to the guide;

a tube for inflating the prosthesis; and a plug at the end of the tube within the prosthesis for sealing the prosthesis.

33. Apparatus for use in laparoscopic techniques comprising:

a tubular sleeve;

a conically shaped guide with a rearward end and an essentially pointed forward end positionable within the sleeve; and a prosthesis coupled to the rearward end of the guide.

34. Apparatus for use in laparoscopic techniques comprising:

a tubular sleeve;

a guide with a rearward end and a forward end positionable within the sleeve; and a prosthesis removably coupled to the rearward end of the guide for movement therewith.

35. Apparatus for use in laparoscopic techniques comprising:

a tubular sleeve;

a guide with a rearward end and a forward end positionable within the sleeve;

an inflatable prosthesis coupled to the guide, the prosthesis having a leading end and a trailing end;

a tube positionable in the rearward end of the prosthesis; and a valve within the trailing end of the prosthesis coaxial with the tube.

* * * * *